United States Patent
Cozzi

(10) Patent No.: US 10,362,785 B2
(45) Date of Patent: Jul. 30, 2019

(54) ACTIVATED HYDROGEN PEROXIDE BIOCIDE COMPOSITION

(71) Applicant: 99 HOLDING S.a.r.l., Luxembourg (LU)

(72) Inventor: Renato Cozzi, Corbetta (IT)

(73) Assignee: 99 HOLDING S.A.R.L., Luxembourg (LU)

(*) Notice: Subject to any disclaimer, the term of this patent is extended or adjusted under 35 U.S.C. 154(b) by 0 days.

(21) Appl. No.: 15/111,116

(22) PCT Filed: Jan. 12, 2015

(86) PCT No.: PCT/IB2015/050215
§ 371 (c)(1),
(2) Date: Jul. 12, 2016

(87) PCT Pub. No.: WO2015/104687
PCT Pub. Date: Jul. 16, 2015

(65) Prior Publication Data
US 2017/0020136 A1  Jan. 26, 2017

(30) Foreign Application Priority Data
Jan. 13, 2014 (IT) .............................. MI2014A0031

(51) Int. Cl.
| | |
|---|---|
| *A01N 59/26* | (2006.01) |
| *A01N 25/02* | (2006.01) |
| *A01N 33/12* | (2006.01) |
| *A01N 57/20* | (2006.01) |
| *A01N 59/00* | (2006.01) |
| *A61L 2/22* | (2006.01) |

(52) U.S. Cl.
CPC ............. *A01N 59/26* (2013.01); *A01N 25/02* (2013.01); *A01N 33/12* (2013.01); *A01N 57/20* (2013.01); *A01N 59/00* (2013.01); *A61L 2/22* (2013.01); *A61L 2202/14* (2013.01); *A61L 2202/25* (2013.01)

(58) Field of Classification Search
CPC ........ A01N 59/26; A01N 25/02; A01N 33/02; A01N 57/20; A01N 59/00
See application file for complete search history.

(56) References Cited

U.S. PATENT DOCUMENTS

| | | | | |
|---|---|---|---|---|
| 2002/0168422 A1* | 11/2002 | Hei | ........................ | A01N 25/02 424/661 |
| 2004/0002616 A1* | 1/2004 | Preto | ...................... | A01N 37/16 562/2 |
| 2005/0152991 A1* | 7/2005 | Man | ........................ | A01N 37/16 424/616 |
| 2008/0139443 A1* | 6/2008 | Buzinski | ................ | C11D 1/835 510/362 |

FOREIGN PATENT DOCUMENTS

| | | |
|---|---|---|
| DE | 3444055 A1 | 6/1986 |
| EP | 0186781 A1 | 7/1986 |
| EP | 1382666 A1 | 1/2004 |
| WO | 91/08981 A2 | 6/1991 |
| WO | 01/65939 A1 | 9/2001 |
| WO | 2010/001319 A1 | 1/2010 |
| WO | 2013/102021 A2 | 7/2013 |

* cited by examiner

*Primary Examiner* — Doan T Phan
(74) *Attorney, Agent, or Firm* — Jeffrey N. Townes; Cozen O'Connor

(57) ABSTRACT

The present invention relates to a disinfectant composition comprising hydrogen peroxide in association with at least one quaternary ammonium salt, suitable for disinfecting a room and the objects that may be therein contained. The composition is further characterized by the absence of ions of heavy metals and is particularly suitable for use in a method for the disinfection of a room, which comprises the diffusion of the present disinfectant composition in the form of a dry mist, maintaining contact with the room and with the objects therein contained, so as to obtain the desired degree of disinfection.

10 Claims, No Drawings

ACTIVATED HYDROGEN PEROXIDE BIOCIDE COMPOSITION

CROSS-REFERENCE TO RELATED APPLICATIONS

This application is a national-stage application under 35 U.S.C. § 371 of PCT Application No. PCT/M2015/050215, filed Jan. 12, 2015, which claims priority to Italian Patent Application No. MI2014A000031 filed Jan. 13, 2014, which are hereby incorporated by reference in their entirety.

The present invention relates in general terms to a disinfectant composition comprising hydrogen peroxide in association with at least one quaternary ammonium salt, which is suitable for the disinfection of a room and the objects that may be contained therein. The invention also relates to a method for the disinfection of a room and the objects that may be therein contained, in particular of healthcare environments such as, for example, laboratories, doctors' surgeries, hospital rooms, and ambulance compartments, as well as interior environments exposed to the public in general, such as public offices, rest homes, classrooms, conference rooms, etc., which comprises the use of the present composition in the form of a disinfectant solution diffused in the rooms in the form of a dry mist.

BACKGROUND ART

In the field of disinfection, the use of hydrogen peroxide- and/or of silver ion-based aqueous solutions as disinfectant/antibacterial compositions has been known for some time.

In this regard, EP1100341 discloses a method and a composition for treating plant matter and foodstuffs in order to prevent the deterioration thereof, also usable for eliminating or reducing the quantity of harmful organisms in farmland, water and also workplaces, surfaces etc. The method envisages the use of an aqueous solution comprising: hydrogen peroxide in a concentration ranging from 0.001% to 50%; dispersed metals or metal ions in an amount comprised from 1 ppb to 5%, with an effective concentration of metal ions selected from copper, zinc, nickel, iron, manganese, molybdenum, potassium and mixtures thereof, less than or equal to 2.5%, and an effective concentration of silver ions less than or equal to 2.5%, as well as the optional addition of additives.

FR 2860721 discloses a method for treating a room by diffusion of a disinfectant liquid in the atmosphere of the room itself, following a precise operating sequence, so as to deliver a sufficient dose of liquid to obtain an effective treatment without going beyond the limits in terms of toxicity and allergenicity of the product.

WO2010001319 discloses a disinfectant composition comprising at least one non-ionic surfactant, in a mixture with silver ions and hydrogen peroxide, suitable for the disinfection of closed environments.

There is also a known system called Nocolyse-Nocospray, where a hydrogen peroxide- and silver ion-based aqueous solution with a bactericidal, virucidal and fungicidal action, which is sprayed and delivered into a room using a delivery device which, by exploiting the Venturi effect, makes it possible to obtain, under certain operating conditions (for example, rather long work times), the formation of a sufficient concentration of oxidizing chemical species capable of destroying microorganisms.

There remains, however, the problem of finding a disinfectant composition which has a high bactericidal and/or fungicidal capacity, a large contact surface and which is capable of performing said action rapidly and at low concentrations, without involving the use of silver ions. The applicants have now found that it is possible to solve the aforesaid problem by means of an aqueous composition comprising hydrogen peroxide and at least one suitable quaternary ammonium salt, and which is suitable as a disinfectant agent for interior environments, in particular for hospital rooms, laboratories, ambulance compartments and the like.

SUMMARY OF THE INVENTION

In a first aspect, the invention relates to a disinfectant aqueous composition comprising: hydrogen peroxide, phosphate and/or hydrogen phosphate and/or phosphonate ions, and at least one ethoxylated and/or propoxylated alcohol, and characterized in that it further comprises at least one quaternary ammonium salt having $C_1$-$C_{22}$ alkyl and/or aryl groups, which may optionally be substituted.

A further aspect of the present invention relates to the use of the above-mentioned aqueous disinfectant composition as a disinfectant agent, in particular for the disinfection of a room and the objects that may be therein contained, preferably by diffusion of the solution in the form of a dry mist.

In an additional aspect the invention also relates to a method for the disinfection of a room and the objects that may be therein contained, which comprises the steps of:

(a) determining the type of microorganisms and the degree of contamination of the room;

(b) determining the volume to be subjected to disinfection, preferably by performing an evaluation of the exposed surfaces, depending on the objects contained in the room itself;

(c) determining, as a function of what was determined according to steps a) and b), a volume concentration of the present disinfectant composition necessary to obtain a predetermined degree of disinfection;

(d) diffusing into the room said aqueous disinfectant composition in the form of a dry mist until obtaining the desired volume concentration;

(e) keeping the aqueous disinfectant composition in the form of a dry mist in contact with the room and the objects that may be therein contained, for a predetermined time so as to obtain the desired degree of disinfection.

DETAILED DESCRIPTION

The term "$C_1$-$C_{22}$ alkyl group" indicates an alkyl residue comprising from 1 to 22 carbon atoms, straight or branched, optionally substituted, for example with phenyl, carbonyl, ester or ether groups or the like.

The term "aryl group" indicates an aromatic residue with 6 carbon atoms, optionally substituted. Analogously, the term "ethoxylated and/or propoxylated $C_{10}$-$C_{18}$ alcohol" indicates an alcohol having from 10 to 18 carbon atoms and having a degree of ethoxylation and/or propoxylation comprised from 2 to 30.

"Quaternary ammonium salt having $C_1$-$C_{22}$ alkyl and/or aryl groups" indicates a quaternary ammonium salt formed from a nitrogen atom substituted with 4 $C_1$-$C_{22}$ alkyl and/or aryl groups, which are identical or different from one another, and having a suitable counterion as defined below in detail.

The term "aqueous solution" is meant to indicate a liquid composition obtained by dissolving the various components in water, and which is substantially free of residues or settling materials such as, for example, precipitates, suspensions or the like.

The term "disinfectant agent" is meant to indicate an agent endowed with bactericidal, virucidal, sporicidal, fungicidal and/or mycobactericidal properties, particularly suitable for the treatment of interior environments such as rooms, chambers and the like, including the objects that may be therein contained.

The present composition, preferably in the form of an aqueous solution, is characterized in that it contains a quaternary ammonium salt which, in association with hydrogen peroxide, is surprisingly capable of imparting very effective disinfectant properties thereto, along with a rapid speed of action. The composition is therefore suitable for the disinfection of rooms and the objects that may be therein contained, such as, for example, hospitals, doctors' surgeries, operating rooms and, in general, healthcare environments in which it is necessary to have a high degree of disinfection, as well as interior environments exposed to the public in general.

In the present disinfectant composition, the preferred quaternary ammonium salts are formed by an atom of cationic nitrogen substituted with $C_1$-$C_{22}$ alkyl and/or aryl groups, which may be identical or different from one another. Said atom of cationic nitrogen has a counterion selected from: bromide ($Br^-$), hydroxyl ($OH^-$) and, preferably, chloride ($Cl^-$).

Particularly preferred are the quaternary ammonium salts selected from: di-n-decyldimethyl ammonium chloride (DDAC), benzalkonium bromide or chloride (benzylalkyldimethylammonium bromide or chloride, CAS No: 7281-04-1, 63449-41-2, respectively) or mixtures thereof. In a preferred embodiment, said salt is di-n-decyldimethyl ammonium chloride (CAS No: 7173-51-5), even more preferably in a mixture with benzalkonium chloride. The selected quaternary ammonium salt is present in the composition in preferred amounts comprised from 0.05 to 2 g/Kg, values comprised from 0.1 to 1 g/Kg being particularly preferred. The applicants have surprisingly found that the presence of at least one quaternary ammonium salt, as described above, together with the specifically selected $C_{10}$-$C_{18}$ ethoxylated/propoxylated alcohols described herein, makes it possible to obtain an excellent wettability of the aqueous composition of the invention, imparting further effective disinfectant properties thereto. In this regard, thanks above all to the quaternary ammonium salt, the present composition shows a high biocidal effectiveness, especially against mould and yeast, ensuring a prolonged time of contact on surfaces and consequently extending the biocidal and biostatic action even beyond the normal treatment times. Moreover, the rapidity of action also shows to be particularly convenient, as demonstrated, for example by the experimental part included herein.

With regard to the concentration of hydrogen peroxide ($H_2O_2$), this is expressed as an actual concentration by weight in the final solution, whereas the concentration of ions is expressed as grams of ions per Kg of final solution (g/Kg). Hydrogen peroxide is used in the present invention with a concentration comprised from 5 to 200 g/Kg, preferably comprised from 10 to 79 g/Kg. The usable hydrogen peroxide (stabilized) is readily commercially available, for example in the form of food or cosmetic grade $H_2O_2$, available for example from EVONIK, ACEF or Elettrochimica Valle Staffora.

The phosphate ($PO_4^{3-}$), hydrogen phosphate ($HPO_4^{2-}$ and/or $H_2PO_4^-$) and/or phosphonate ($HPO_3^{2-}$ and/or $H_2PO_3^-$) ions can be present in a quantity comprised from 0.01 to 2 g/Kg, preferably from 0.02 to 1 g/Kg. They can be introduced into the present disinfectant composition by addition of: a phosphate salt and/or acid, alkaline or alkaline earth phosphate; a water-soluble diphosphonic acid or derivate; or by adding phosphoric acid $H_3PO_4$, or mixtures thereof. In a preferred embodiment, the composition of the invention comprises hydroxyethylidene diphosphonic acid (CAS No. 2809-21-4), and/or $KH_2PO_4$, even more preferably in overall amounts comprised from 0.04-0.4 g/Kg.

In this regard, it is believed that the phosphate and/or hydrogen phosphate and/or phosphonate ions perform a stabilizing effect for hydrogen peroxide. In particular, it is believed that the introduction of said ions enables an optimal pH adjustment with the formation of a buffered solution with an acidic pH, at a value whereby the hydrogen peroxide is more stable and has a particularly high oxidizing capacity. Therefore, in one embodiment of the invention, the pH of the disinfectant composition is adjusted to values of less than 5, even more preferably comprised from 1 to 4, values comprised from 2 to 3 being particularly preferred. The pH adjustment can be made by addition of a phosphoric derivate as described above, and/or by further addition of an acid compatible with the composition, preferably phosphoric acid.

The ethoxylated and/or propoxylated components of the present composition have an EO or an OP (understood as degree of ethoxylation or of propoxylation) comprised from 2 to 30 mol, preferably from 4 to 22. Preferably, the present aqueous disinfectant composition comprises a mixture of ethoxylated alcohols having from 8 to 18 carbon atoms ($C_8$-$C_{18}$). By way of example, "ethoxylated alcohol 20 mol EO" indicates a fatty alcohol (understood as having at least 8 carbon atoms) made to react with 20 moles of ethylene oxide, in such a way as to yield a long chain of atoms —C—O—C—.

In a preferred embodiment, the composition comprises a C10 ethoxylated alcohol 6 mol EO (available, for example, as Greenbenin-DE/060 Gamma Chimica), in admixture with sorbitan monolaurate 20 mol EO (for example Tween 20 or Kotilen-L/1 Gamma Chimica). The applicants have found that the presence of said mixture contributes to improving the spraying process for the disinfectant solution, enabling a larger contact surface and smaller doses. The ethoxylated and/or propoxylated derivates are preferably present in the composition in amounts comprised from 0.05 to 2.0 g/Kg, even more preferably comprised from 0.1 to 1.0 g/Kg.

In one embodiment, the present composition comprises the following components in the specified amounts:

| | |
|---|---|
| Quaternary ammonium salt or salts with $C_1$-$C_{22}$ alkyl and/or aryl substituents. | 0.05-2 g/Kg (overall concentration) |
| Stabilized $H_2O_2$ | 10-79 g/Kg |
| phosphate and/or hydrogen phosphate ions | 0.04-0.8 g/Kg |
| $C_{10}$-$C_{18}$ ethoxylated and/or propoxylated alcohols, 4-22 mol EO | 0.05-2 g/Kg |
| Water, preferably pharamacopoeia grade purified water | q.s. to 1 Kg |
| Phosphoric acid | q.s. to pH 2-3 |

Optionally, the present composition may also contain at least one $C_1$-$C_{12}$ aliphatic and/or aromatic organic acid with a low molecular weight, preferably in amounts of between 0.005 and 0.5 g/Kg.

In a preferred embodiment, the present composition comprises:

| | |
|---|---|
| Di-n-decyldimethyl ammonium chloride | 0.1-1.0 g/Kg |
| Benzalkonium chloride | 0.01-0.10 g/kg |
| Stabilized $H_2O_2$ | 50-79 g/Kg |
| Hydroxyethylidene diphosphonic acid | 0.02-0.10 g/Kg |
| Ethoxylated alcohol C10, 6 mol EO | 0.2-0.6 g/Kg |
| Sorbitan monolaurate, 20 mol EO | 0.01-0.02 g/Kg |
| Salicylic acid | 0.02-0.08 g/Kg. |
| Water, deionized or preferably pharamacopoeia grade purified water | q.s. to 1 Kg |
| Phosphoric acid | q.s. to pH 2-3 |

The composition of the invention in the form of an aqueous solution can be prepared by mixing, in water, preferably pharmacopoeia grade highly purified water, the quaternary ammonium salt, the source of phosphate and/or hydrogen phosphate ions, the hydrogen peroxide and the ethoxylated and/or propoxylated alcohols, under stirring at room temperature (i.e. comprised from about 15° C. to about 40° C.). Advantageously, the disinfectant aqueous solution obtained has a high disinfecting power, combined with a high rapidity of action, as demonstrated by the experimental part included herein. The present composition is moreover characterized in that it does not comprise ions of heavy metals, such as silver, copper, zinc and the like, making it easily applicable also on a large scale, substantially avoiding the typical toxicological problems that may derive from the presence of said metals.

A further aspect of the invention relates to a method for the disinfection of a room and the objects that may be therein contained, which comprises the steps of:

(a) determining the type and degree of contamination of the room caused by microorganisms;

(b) determining the volume of the room to be subjected to disinfection, and performing an evaluation of the exposed surfaces, depending on the objects contained in the room itself;

(c) determining, as a function of what was determined according to steps a) and b), and depending on the degree of disinfection it is desired to obtain, a volume concentration of the present aqueous solution diffused in the room in the form of a dry mist;

(d) diffusing into the room said aqueous disinfectant composition in the form of a dry mist;

(e) keeping the aqueous disinfectant composition in the form of a dry mist in contact with the room and the objects that may be therein contained, for a predetermined time so as to obtain the desired degree of disinfection.

The determination of the type and degree of contamination of the room to be disinfected and of the effectiveness of the disinfection treatment can be based on methods, well known in the art, of culturing the microorganisms of interest so as to obtain a count of the viable microorganisms, expressed as $CFU/cm^2$.

The effectiveness of the disinfection treatment can be evaluated by means of the reduction in viability (R):

$$R = \frac{Nv}{Na}$$

where:
$N_v$=CFU on the sample surface prior to the treatment;
Na=CFU on the sample surface after the treatment.

On the basis of the trials conducted by the Applicant, it was found that the volume concentration of the disinfectant solution in the form of a dry mist of step c) is preferably comprised from about 0.5 $ml/m^3$ to 30 $ml/m^3$, more preferably from about 1 $ml/m^3$ to 10 $ml/m^3$.

In one embodiment, the disinfectant solution in the form of a dry mist is made up of microdroplets having an average size of less than about 5 μm (micrometers), preferably less than about 3 μm (micrometers).

To this end, the process of diffusion within the room according to step d) can be conducted, for example, with an atomizing device used in the art, and known to the person skilled in the art (for a general reference see WO2005/025757). Preferably, the delivery speed is comprised from about 70 meters per second (m/sec) to 90 m/sec. The delivery pressure during step d) is usually set in such a way as to obtain a temperature of the disinfectant solution sprayed in the form of a dry mist preferably comprised from about 5° C. to about 40° C.

With regard to step (e), the time of contact of the sprayed solution with the room to be disinfected is generally comprised from about 5 minutes to about 120 minutes, preferably from about 10 minutes to about 60 minutes.

The present invention will now be described with the following non-limiting experimental part.

EXPERIMENTAL PART

Example 1

Use of the Composition of the Invention as an Antibacterial Agent

A series of test were performed on one composition of the invention (indicated as 99Q) comprising:

| Component | Amount |
|---|---|
| Di-n-decyldimethyl ammonium chloride | 0.400-0.600 g/Kg |
| Stabilized $H_2O_2$ | 75-79 g/Kg |
| Hydroxyethylidene diphosphonic acid | 0.020-0.050 g/Kg |
| Ethoxylated alcohol C10, 6 mol EO (Deceth 10) | 0.200-0.450 g/Kg |
| Sorbitan monolaurate, 20 mol EO | 0.010-0.030 g/Kg |
| Pharamacopoeia grade purified water | q.s. to about 1 Kg |
| Phosphoric acid | q.s. to obtain a pH of about 2-3 |

The bactericidal effectiveness of the above composition 99Q was verified against the bacteria *Staphylococcus aureus* ATCC6538 and *Pseudomonas aeruginosa* ATCC15442, in suspensions having concentrations comprised from $1.5 \times 10^6$ to $5.0 \times 10^6$ CFU/ml, diluted to $10^{-4}$ and $10^{-5}$. Said bacteria were exposed under the following conditions:

Contact time: 5 minutes
Test temperature: 20° C.
Interfering substance: bovine albumin, 0.03% solution (final concentration).

The tests demonstrated that the disinfectant composition 99Q caused a >4 Log reduction of *Staphylococcus aureus* ATCC6538 and *Pseudomonas aeruginosa* ATCC15442 after 5 minutes of contact using bovine albumin with a final concentration of 0.03%, in accordance with the standard currently in force, EN13697:2001.

Example 2

Use of the Composition of the Invention as an Antifungal Agent

The antifungal effectiveness of composition 99Q of Example 1 was verified against the fungal strain *Aspergillus* niger ATCC16404, in suspensions having concentrations comprised from $1.5 \times 10^7$ to $5.0 \times 10^7$ CFU/ml, diluted to $10^{-5}$ and $10^{-6}$. Said bacteria were exposed under the following conditions:

Contact time: 15 minutes
Test temperature: 20° C.
Interfering substance: bovine albumin, 0.03% solution (final concentration).

The tests demonstrated that disinfectant composition 99Q caused a >3 Log reduction of *Aspergillus niger* ATCC16404, after 5 minutes of contact using bovine albumin with a final concentration of 0.03%, in accordance with the standard currently in force, EN13697:2001.

Example 3

Use of the Composition of the Invention in the Form of a Dry Mist as a Disinfectant Agent for Rooms The disinfectant antifungal activity of composition 99Q of the invention was tested by spraying said composition in the form of a dry mist in a room containing objects exposed to the strain *Aspergillus niger*.

Test conditions:
Contact time (99.99M micro-nebulizer modulator): 3 hours starting from the end of spraying,
Spraying time: 19 minutes,
Distance between spraying device and contaminated objects: the objects were placed in three points of the room, on the side opposite that of the spraying device, at a distance of about 2.6 m.
Room volume: 39.2 cubic meters
Test temperature: comprised from 20° C. to 22° C., approximately.

The test demonstrated that the present composition sprayed in the form of a dry mist is capable of causing a >4 Log reduction of *Aspergillus niger*, in line with the requirements of the AFNOR NF T 72-281:2009 method.

The results obtained are summarized in the table below:

| MICROORGANISM | CONCENTRATION*/ CONTACT TIMES | Log (Reduction in antibacterial action) |
|---|---|---|
| *Staphylococcus aureus* ATCC6538 (Example 1) | 100%/5 minutes | >6.97 |
| *Pseudomonas aeruginosa* ATCC15442 (Example 1) | 100%/5 minutes | >6.07 |
| *Aspergillus niger* ATCC16404 (Example 2) | 100%/15 minutes | >6.36 |
| *Aspergillus niger* ATCC16404 (Example 4) | 100%/19 min + 3 hours | >4.25 |

*A 100% concentration means that composition 99Q of Example 1 is used without further dilutions.

The invention claimed is:

1. An aqueous composition consisting essentially of:
0.1-1 g/kg Di-n-decyldimethyl ammonium chloride,
0.01-0.10 g/kg benzalkonium chloride,
50-79 g/kg stabilized $H_2O_2$,
0.02-0.10 g/kg hydroxyethylidene diphosphonic acid,
0.2-0.6 g/kg $C_{10}$ethoxylated alcohol having a degree of ethoxylation of 6 mol,
0.01-0.02 g/kg sorbitan monolaurate having a degree of ethoxylation of 20 mol,
up to 1 kg deionized or purified water, and
a sufficient amount of phosphoric acid to reach a pH between 2-3;
wherein the aqueous composition is in the form of a dry mist made up of microdroplets having an average size of less than 5 μm.

2. The aqueous composition according to claim 1, further comprising $KH_2PO_4$.

3. The aqueous composition according to claim 1, further comprising 0.02-0.08 g/kg salicylic acid.

4. The aqueous composition according to claim 1, wherein the microdroplets have an average size of less than 3 μm.

5. A method of using the aqueous composition according to claim 1 as a bactericidal, virucidal, sporicidal, fungicidal and/or mycobactericidal agent, comprising the step of contacting an object with the aqueous composition, wherein the aqueous composition acts as a bactericidal, virucidal, sporicidal, fungicidal and/or mycobactericidal agent.

6. A method of using the aqueous composition according to claim 1 for the disinfection of a room and of any objects contained therein, comprising the step of diffusing the aqueous composition in the form of a dry mist into the room, wherein the aqueous composition acts as a disinfectant.

7. A method for the disinfection of a room and objects contained therein, comprising the steps of:
a) determining the type and degree of contamination of the room caused by microorganisms;
b) determining the volume of the room to be subjected to disinfection by performing an evaluation of exposed surfaces on the objects contained in said room;
c) determining, as a function of what was determined according to steps a) and b) and as a function of the desired degree of disinfection, the volume concentration of a disinfectant composition comprising the aqueous composition according to claim 1;
d) diffusing into the room said aqueous disinfectant composition in the form of a dry mist, up to the desired volume concentration; and
e) keeping said aqueous disinfectant composition in the form of a dry mist in contact with the room and the objects contained therein, for a predetermined time so as to obtain the desired degree of disinfection.

8. The method according to claim 7, wherein the volume concentration of the aqueous disinfectant composition in the form of dry mist of step d) is between 0.5 and 30 ml/m³.

9. The method according to claim 7, wherein the step d) of diffusion is carried out at a diffusion rate of the aqueous disinfectant composition ranging from 70 m/sec to 90 m/sec.

10. The method according to claim 9, wherein the aqueous disinfectant composition in the form of dry mist of step d) has a temperature ranging from 5° C. to 40° C.

* * * * *